United States Patent [19]

Shaw

[11] 4,185,632
[45] Jan. 29, 1980

[54] SURGICAL INSTRUMENT HAVING SELF-REGULATED ELECTRICAL SKIN-DEPTH HEATING OF ITS CUTTING EDGE AND METHOD OF USING THE SAME

[76] Inventor: Robert F. Shaw, 50 St. Germain, San Francisco, Calif. 94114

[21] Appl. No.: 558,335

[22] Filed: Mar. 14, 1975

Related U.S. Application Data

[63] Continuation-in-part of Ser. No. 534,756, Dec. 2, 1974, Pat. No. 4,089,336, which is a continuation of Ser. No. 63,645, Aug. 13, 1970, abandoned, which is a continuation of Ser. No. 681,737, Nov. 9, 1967, abandoned.

[51] Int. Cl.$^2$ .............................................. A61B 17/32
[52] U.S. Cl. .................................. 128/303.1; 30/140; 219/233
[58] Field of Search .......... 30/140; 128/303.1, 303.13, 128/303.14; 219/221, 223, 227, 228, 229, 230, 231, 233, 241

[56] References Cited

U.S. PATENT DOCUMENTS

| 3,489,884 | 1/1970 | Waseleski, Jr. ............... 219/241 UX |
| 3,584,190 | 6/1971 | Marcoux ................................ 219/233 |
| 3,768,482 | 10/1973 | Shaw ................................ 128/303.1 |
| 3,826,263 | 7/1974 | Cage et al. ......................... 128/303.1 |

Primary Examiner—Robert W. Michell
Assistant Examiner—Michael H. Thaler
Attorney, Agent, or Firm—Lyon & Lyon

[57] ABSTRACT

The cutting edge of a scalpel blade is resistively heated to a preselected constant temperature range by conduction of high frequency electrical currents within variable skin depths of a ferromagnetic conductor that is disposed on the blade in the region of the cutting edge.

27 Claims, 2 Drawing Figures

SURGICAL INSTRUMENT HAVING SELF-REGULATED ELECTRICAL SKIN-DEPTH HEATING OF ITS CUTTING EDGE AND METHOD OF USING THE SAME

RELATED APPLICATIONS

This application is a continuation-in-part of U.S. patent application Ser. No. 534,756 filed Dec. 2, 1974, now U.S. Pat. No. 4,089,336 which is a continuation of U.S. patent application Ser. No. 63,645 filed Aug. 13, 1970, now abandoned, which is a continuation of U.S. patent application Ser. No. 681,737 filed Nov. 9, 1967, now abandoned.

BACKGROUND OF THE INVENTION

The control of bleeding during surgery accounts for a major portion of the total time involved in an operation. The bleeding that occurs from the plethora of small blood vessels that pervade all tissues whenever tissues are incised obscures the surgeon's vision, reduces his precision, and often dictates slow and elaborate procedures in surgical operations. It is well known to heat the tissues to minimize bleeding from incisions, and surgical scalpels which are designed to elevate tissue temperatures and minimize bleeding are also well known. One such scalpel transmits high frequency, high energy sparks from a small electrode held in the surgeon's hand to the tissues, where they are converted to heat. Typically, substantial electrical currents pass through the patient's body to a large electrode beneath the patient, which completes the electrical circuit. Discharge of sparks and temperature conversion in the tissue are poorly controlled in distribution and intensity, and erratic muscular contractions in the patient are produced so that this apparatus cannot be used to perform precise surgery. Further, apparatus of this type frequently produce severe tissue damage and debris in the form of charred and dead tissue, which materially interfere with wound healing.

Another well-known surgical scalpel employs a blade with a resistive heating element which cuts the tissue and provides simultaneous hemostasis. Although these resistive elements can be readily brought to a suitably high and constant temperature in air prior to contacting tissues, as soon as portions of the blade come in contact with tissues, they are rapidly cooled. During surgery, non-predictable and continuously varying portions of the blade contact the tissues as they are being cut. As the blade cools, the tissue cutting and hemostasis become markedly less effective and tissue tends to adhere to the blade. If additional power is applied by conventional means to counteract this cooling, this additional power is selectively delivered to the uncooled portions of the blade, frequently resulting in excessive temperatures which may result in tissue damage and blade destruction. This results from the fact that in certain known resistively heated scalpels, the heating is a function of the current squared times the resistance ($I^2R$). In conventional metallic blades of this type, the higher the temperature of any blade portion, the greater its electrical resistance, and consequently the greater the incremental heating resulting from incremental power input.

It is generally recognized that to seal tissues and effect hemostasis it is desirable to operate at a temperature between 300° C. and 1000° C. And for reasons noted above, it is desirable that electrothermal hemostatic surgical cutting instruments include a mechanism by which power is selectively delivered to those portions of the blade that are cooled by tissue contact so that the cutting edge may be maintained at a substantially uniform operating temperature within the desired optimal range. Recently, hemostatic scalpels have been described (see, for example, U.S. Pat. Nos. 3,768,482 and 3,826,263) in which the temperature-controlling mechanisms include resistive heating elements disposed on the surface of the scalpel blade. However, such instruments require precision in fabricating the dimensions of the heating elements to obtain the desired resistances. And such resistive heating elements may be subjected to variations in resistance during use, as tissue juices and proteins become deposited upon the surface of the blade.

SUMMARY OF THE INVENTION

The present invention provides a surgical cutting instrument in which the cutting portion of the blade is brought to and maintained within an elevated preselected temperature range by heating due to radio frequency electrical current flowing within variable skin depths in an electrical conductor disposed in the region of the cutting edge. Radio frequency alternating current is conducted by the current-carrying conductor disposed near the cutting edge of the blade. The current tends to concentrate near the surface and to attenuate exponentially with distance from the surface. This phenomenon is called "skin effect". The depth of this skin effect is the depth at which the current is reduced to about 37% of its surface value and is determined by the electrical resistivity and magnetic permeability of the material conducting the current and by the frequency of the alternating current. The skin depth d, in centimeters, is determined by $$d = 5(10^3)\sqrt{\frac{\rho}{\mu f}},$$

where $\rho$ is electrical resistivity in ohm-centimeters, $\mu$ is relative magnetic permeability, and f is frequency in hertz.

A self-regulating heated scalpel is constructed by causing radio frequency (RF) current to flow in conductors utilized as resistive heating elements which are disposed in the region of the cutting edge of the scalpel and which are constructed of a material that exhibits an increase in an electrical parameter such as magnetic permeability as the temperature decreases. It can be seen that an increase in magnetic permeability causes a decrease in the skin depth. Since the resistance of the current-conducting path is inversely proportional to cross-sectional area (path width times skin depth), this effect causes an increase in the resistance of the current path in cooled regions and an increase in the Joule heating thereof.

By way of example, ferromagnetic material such as iron, nickel, and cobalt, and their alloys exhibit large changes in relative permeability as their temperature goes through a transition point called the "Curie" point. For many iron-nickel alloys this Curie point occurs at about 450° C., above which the relative permeability is near unity and below which it is high, perhaps 100 to 1000, for the magnetic field strengths that would be utilized in this application. An applied RF signal causes current to flow in the surface conductor of the blade near the cutting edge which heats the edge to about 500° C. prior to contact with tissues. When portions of the cutting edge are cooled upon contact with tissues, the cooled portions may drop in temperature below the Curie point and this will increase the relative permeability from near unity to above 100. The associated skin depth will decrease more than 10 to 1 and heating will increase proportionately in the cooled portion.

In accordance with the present invention, a scalpel blade of electrically insulating material such as alumina ceramic is electrically heated in the region of the cutting edge thereof by conducting high frequency current along conductors near the cutting edge, which conductors are formed of ferromagnetic material disposed on the insulating material of the blade.

DESCRIPTION OF THE PREFERRED EMBODIMENT

Figure 1:
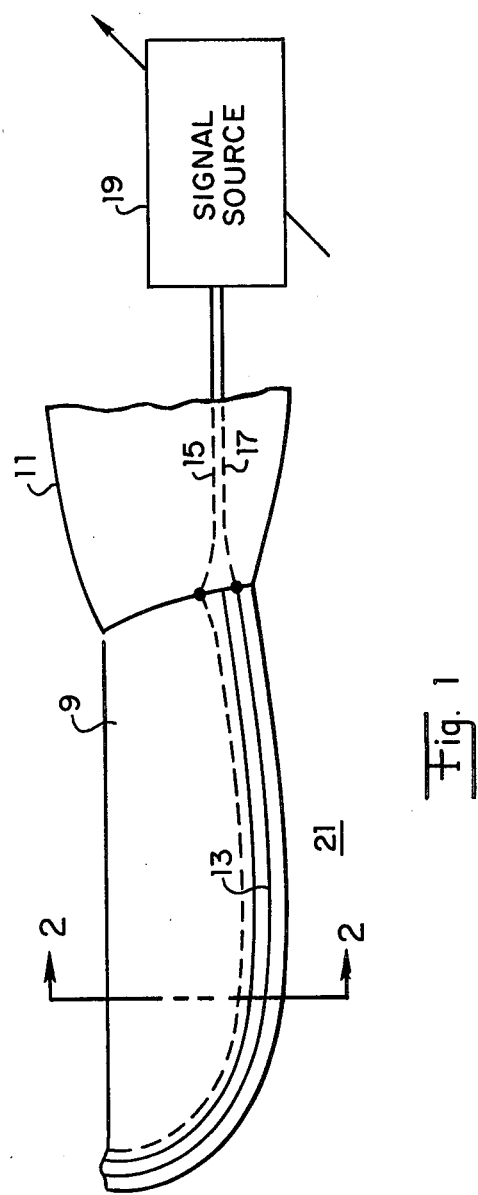
FIG. 1 is a side view of the surgical instrument according to the present invention.
Figure 2:
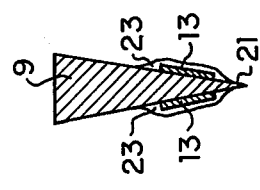
FIG. 2 is an end sectional view of the blade of the apparatus of FIG. 1.

Referring now to FIGS. 1 and 2 there is shown one embodiment of the present invention including a blade portion 9 of electrically insulating material such as alumina ceramic attached to a handle portion 11 to form the surgical instrument. A signal conductor 13 of ferromagnetic material such as nickel-iron is disposed on the blade 9 adjacent the cutting edge 21 to form a complete conduction path along one side of the blade 9 and back along the other side of the blade. Input power at radio frequencies may be supplied to the conductor 13 from power source 19 through connection means 15 and 17.

With the current-carrying conductor 13 formed of ferromagnetic material, the skin depth characteristic previously discussed can be utilized advantageously for temperature regulation. Current flowing through the ferromagnetic conductor 13 will flow on the inside of the conductor at the skin depth for the material and heat the ferromagnetic material and the ceramic cutting edge 21 thermally coupled thereto. From an operating temperature in air which is above the Curie temperature, portions of the cutting edge will cool as it touches tissue and its operating temperature may drop below the Curie temperature and the skin depth will decrease about 10 to 1 giving approximately a 10 to 1 local increase in heating. To achieve a 10 to 1 power increase, not only must the relative permeability increase 100 to 1 when cooled by tissue contact, but also the skin depth at pre-cutting operative conditions in air must be approximately two-thirds the thickness of the conductor or less in order to realize the 10 to 1 skin depth reduction. Thus, for a suitably thin scalpel blade with a suitably thin ferromagnetic self-regulating conductive heater disposed upon it, high frequencies may be required to establish the requisite skin depths. The following tabulation shows the frequency required for various skin depths above and below the Curie point in a 50:50 iron-nickel ferromagnetic alloy and shows the relative power dissipation of a 40 mil wide conductor disposed continuously upon both facets of a scalpel blade in the region of a 3 cm. cutting edge when energized by a current of about 3 amperes:

| Temperature °C. | Resistivity ohms-cm($10^{-6}$) | Permeability | Frequency MHz | Skin Depth mils (inch $\times 10^{-3}$) | Resistance ohms | Power watts/cm of cutting edge |
|---|---|---|---|---|---|---|
| 500 | 105 | 1 | 6 | 8.3 | .29 | .88 |
| 500 | 105 | 1 | 20 | 4.5 | .54 | 1.61 |
| 500 | 105 | 1 | 100 | 2.0 | 1.20 | 3.61 |
| 400 | 100 | 100 | 6 | 0.81 | 2.87 | 8.62 |
| 400 | 100 | 100 | 20 | 0.44 | 5.25 | 15.7 |
| 400 | 100 | 100 | 100 | 0.20 | 11.7 | 35.2 |

A layer of insulation 23 is disposed over the conductors 13 to insulate the tissue being cut from the electrical currents.

The high frequency signal source 19 may be adjustable in signal amplitude or in frequency, or both, to adjust the average operating temperature of the cutting edge. The frequency may be adjusted to alter the skin depth, as described above, and thereby to establish the ambient operating temperature of the cutting edge in air.

I claim:

1. A blade comprising:
   a cutting means including a cutting edge; and
   electrical conductor means disposed near said cutting edge, said electrical conductor means including a material being capable of varying the skin depth of the conducting path for alternating electrical current therethrough.

2. A blade as in claim 1 wherein the material of said electrical conductor means exhibits a Curie point transition in permeability.

3. A blade as in claim 1 wherein said material of the electrical conductor means is ferromagnetic material.

4. A blade as in claim 1 wherein said material of the electrical conductor means includes an element selected from the group consisting of iron, nickel and cobalt.

5. A blade as in claim 1 comprising a layer of insulated material disposed over said electrical conductor means.

6. The blade claimed in claim 1 wherein said blade includes a ceramic.

7. A blade as in claim 1 further comprising an alternating signal source connected to said electrical conductor for supplying power thereto.

8. A blade as in claim 1 further comprising:
   means responsive to the temperature of a region along said cutting edge for producing a representative control signal; and
   means responsive to said control signal for altering a selected parameter of the alternating signal applied to said electrical conductor means from said source.

9. A cutting instrument as in claim 1 wherein the frequency of the applied alternating signal is altering in response to the control signal.

10. A blade comprising:

a cutting edge and;
electrical conductor means disposed near said cutting edge, wherein said material of said electrical conductor means includes an element selected from the group consisting of iron, nickel and cobalt and exhibits a Curie point transition in permeability within the range of temperatures from about 300° C. to about 1,000° C.

11. The blade claimed in claim 10 further comprising a layer of insulating material disposed over said electrical conductor means.

12. The method of cutting using a blade means having a cutting edge operating at an elevated temperature, the method comprising:
heating the cutting edge by an alternating electrical current in a conduction path; and
automatically reheating the cutting edge by decreasing the skin depth in regions of the conduction path in response to a cooling of the edge in said regions.

13. The method of cutting as in claim 12 wherein the conduction path includes a material which has a permeability that varies inversely with temperature to decrease the cross-sectional area of the conduction path.

14. The method of cutting as in claim 12 comprising altering the frequency of the alternating electrical current in response to changes in temperature along the cutting edge to vary the cross-sectional area of the conduction path.

15. A hemostatic surgical blade comprising:
a cutting means including a tissue cutting edge capable of operating at an elevated temperature; and
electrical conductor means disposed near said cutting edge, said electrical conductor means including a material being capable of varying the skin depth of the conducting path for alternating electrical current therethrough.

16. A surgical blade as in claim 15 wherein said electrical conductor means includes a material having a permeability which varies inversely with temperature over a selected temperature range.

17. A surgical blade as in claim 15 wherein said material of said electrical conductor means exhibits a Curie point transition in permeability within the range of temperatures from about 300° C. to about 1000° C.

18. A surgical blade as in claim 15 wherein said material of said electrical conductor is a ferromagnetic material.

19. A surgical blade as in claim 15 wherein said material of the electrical conductor means includes an element selected from the group consisting of iron, nickel and cobalt.

20. A surgical blade as in claim 15 comprising a layer of insulated material disposed over said electrical conductor means to insulate tissued being cut from electrical shock.

21. A surgical blade for cutting tissue with simultanoues hemostasis comprising:
a cutting means including a tissue cutting edge; and
electrical conductor means disposed near said tissue-cutting edge, wherein said material of said electrical conductor means includes an element selected from the group consisting of iron, nickel and cobalt and exhibits a Curie point transition in permeability within the range of temperatures from about 300° C. to about 1,000° C.

22. The surgical blade claimed in claim 21 further comprising a layer of insulating material disposed over said electrical means to insulate tissue being cut from said surgical instrument.

23. The surgical blade claimed in claim 21 herein said blade includes a ceramic.

24. A surgical method of cutting tissue using a blade means having a cutting edge operating at an elevated temperature, the method comprising:
heating the cutting edge by an alternating electrical current in a conduction path; and
automatically reheating the cutting edge by decreasing the skin depth in regions of the conduction path in response to a cooling of the edge in said regions.

25. The surgical method of cutting tissue as in claim 24 wherein the conduction path includes a material which has a permability that varies inversely with temperature to decrease the skin depth of the conduction path.

26. The surgical method of cutting tissue as in claim 24 comprising altering the frequency of the alternating electrical current in response to changes in temperature along the cutting edge to vary the skin depth of the conduction path.

27. A blade as in claim 1 wherein said conduction path is utilized to elevate the temperature in the region of the cutting edge.

* * * * *